US005293008A

United States Patent [19]

Danielsen

[11] Patent Number: 5,293,008

[45] Date of Patent: Mar. 8, 1994

[54] EARWAX TRAP FOR USE WITH HEARING-AID APPARATUS, AND HEARING-AID APPARATUS WITH SUCH A TRAP

[75] Inventor: Finn Danielsen, Lyngby, Denmark

[73] Assignee: Oticon A/S, Denmark

[21] Appl. No.: 910,271

[22] PCT Filed: Feb. 20, 1991

[86] PCT No.: PCT/DK91/00051

§ 371 Date: Jul. 21, 1992

§ 102(e) Date: Jul. 21, 1992

[87] PCT Pub. No.: WO91/13525

PCT Pub. Date: Sep. 5, 1991

[30] Foreign Application Priority Data

Feb. 26, 1990 [DK] Denmark .............................. 499/90

[51] Int. Cl.[5] .............................................. A61B 7/02

[52] U.S. Cl. .................................................... 181/135

[58] Field of Search .................. 181/130, 135; 381/68, 381/68.6, 69

[56] References Cited

U.S. PATENT DOCUMENTS 4,553,627 11/1985 Gastmeier et al. .................. 181/135

4,870,689 9/1989 Weiss .................................. 181/135

4,953,215 8/1990 Weiss et al. ...................... 181/135 X

*Primary Examiner*—Michael L. Gellner

*Assistant Examiner*—Khanh Dang

*Attorney, Agent, or Firm*—Larson & Taylor

[57] ABSTRACT

A earwax trap used with hearing-aid apparatus comprises a) in a first part (6) a space (8) adapted to communicate acoustically an interior part of the hearing-aid apparatus with the external auditory meatus of the user's ear, and b) an arrangement for preventing earwax having entered the space (8) from leaving same towards the interior part (3). The latter arrangement comprises at least one piston- or plug-shaped member (7), which is adapted by relative movement between itself and the first part (6) containing the space (8) to enter that space (8) in a first direction away from the interior part of the hearing-aid apparatus, and to leave the space (8) in the opposite direction and thus re-establish the acoustic connection between the interior part and the space (8). In this manner, earwax (15) having collected in the space (8) communicating with the user's external auditory meatus, can be expelled without using an external device, such as pipe cleaners or the like, and without risk of damage to the internal parts of the hearing aid.

12 Claims, 3 Drawing Sheets

EARWAX TRAP FOR USE WITH HEARING-AID APPARATUS, AND HEARING-AID APPARATUS WITH SUCH A TRAP

TECHNICAL FIELD

The present invention relates to an earwax trap of the kind wherein, in first part, a space is provided which is adapted to afford acoustical communication between an interior part of hearing-aid apparatus and the external auditory meatus of the user's ear and a means is provided for preventing earwax that has entered the space from exiting from that space into the interior part.

BACKGROUND ART

Earwax traps of this kind are known from the European Patent Application No. 0 326 513 and Japanese Patent Publication No. 55-61194. In the earwax traps thus known, there are no means to remove the earwax, which has to be removed by external means, such as pipe cleaners or the like, which may damage the earwax trap and/or internal parts of the hearing-aid apparatus, such as the so-called receiver converting electric signals into sound.

DISCLOSURE OF THE INVENTION

It is the object of the present invention to provide an earwax trap of the kind initially referred to, in which the earwax may be removed without using external means, and this object is achieved with an earwax trap comprising means for preventing ear wax that has entered the space referred to above from exiting from that space into the interior part of the hearing-aid apparatus in the form of at least one piston- or plug-shaped member, which is adapted by relative movement between itself and the first part containing said space, to enter said space in a first direction away from said interior part of said hearing-aid apparatus, and to leave said space in a direction opposite to said first direction and thus reestablish the acoustic connection between said interior part and said space. The piston- or plug-shaped member is always present in the earwax trap, and when it is moved in the first direction mentioned in the claim, it will push any earwax having collected of out the trap, and when it is moved in the opposite direction, it no longer constitutes an obstruction in the acoustical path.

Specific advantageous embodiments of the earwax trap according to the present invention, are described below, the effects of which embodiments are explained in more detail in the following detailed portion of the present specification.

The present invention also relates to a hearing-aid apparatus of the kind with an earwax trap, the earwax trap comprising a) in a first part, a space adapted to provide an acoustic connection between an interior part of the hearing-aid apparatus and the external auditory meatus of the user's ear, and b) means for preventing earwax after having entered said space from leaving said space towards said interior part, c) said means comprising at least one piston- or plug-shaped member, which is adapted by relative movement between itself and the first part containing said space, to enter said space in a first direction away from said interior part of said hearing-aid apparatus, and to leave said space in a direction opposite to said first direction and thus reestablish the acoustic connection between said interior part and said space.

BRIEF DESCRIPTION OF THE DRAWINGS

In the following detailed specification, the invention will be explained in more detail with reference to various embodiments of earwax traps according to the invention shown in the drawing, in which.

DESCRIPTION OF THE PREFERRED EMBODIMENT(S)

Figure 1:
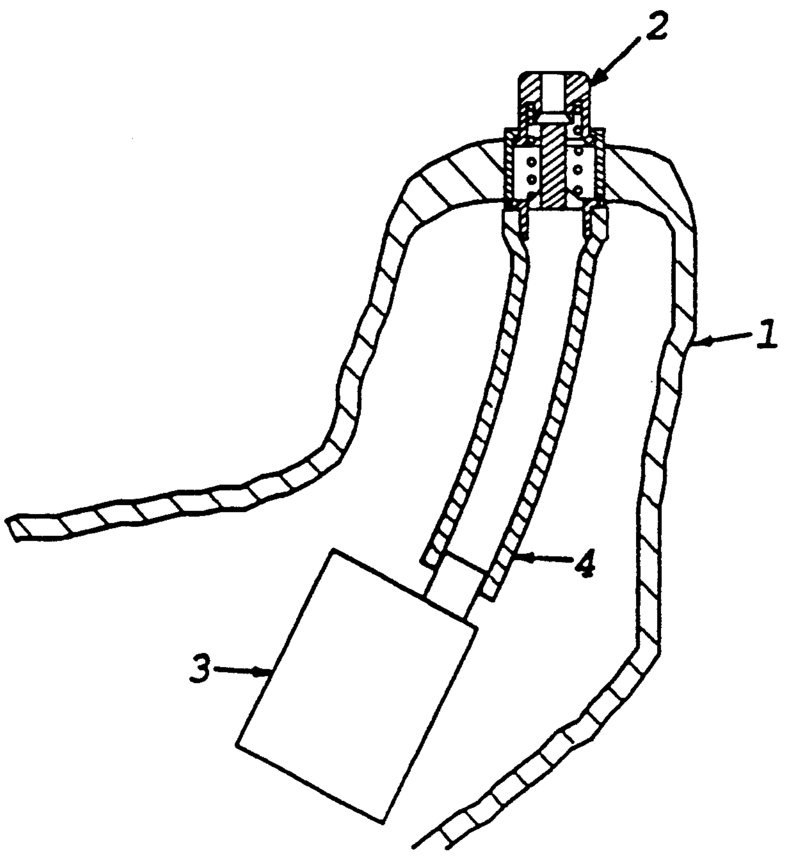
FIG. 1 is a sectional view through a part of a hearing-aid apparatus incorporating an earwax trap according to a first embodiment of the present invention.

FIG. 1 shows an insertion portion 1 of a hearing-aid apparatus, of which only the components relevant to the present invention are shown, i.e.

- said insertion portion 1,
- a connecting piece 2 constituting an acoustical connection through the wall of the tip of said insertion portion 1,
- an electro-acoustical transducer or receiver 3 adapted to generate sound in response to electrical signals from a microphone and amplifier (not shown) associated with or constituting part of the hearing-aid apparatus, and
- a connecting tube 4 constituting an acoustical connection from the receiver 3 to the connection piece 2.

Apart from serving as an acoustical conductor through the wall of the insertion portion 1, the connecting piece 2 is also adapted to prevent earwax from the user's external auditory meatus from entering and eventually blocking the acoustical conduit leading from the receiver 3 to the outside of the insertion portion 1, in a manner to be explained in more detail below. For this reason; the connecting piece 2 is also designated "earwax trap", which designation will be used in the remainder of the present specification.

Figure 2:
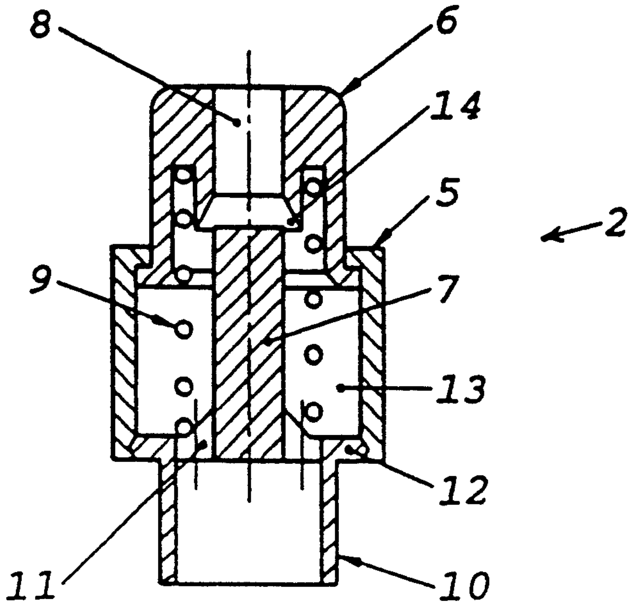
FIG. 2 is an enlarged sectional view of the earwax trap shown in FIG. 1, FIG. 3 *a–c* are sectional views illustrating the functioning of the earwax trap, and FIG. 4 *a–f* are sectional views of various possible practical variations of an earwax trap according to said first embodiment, and FIG. 5 *a, b* are sectional views showing an earwax trap according to a second embodiment of the present invention in operating and wax-removal positions respectively.

Referring now to FIG. 2, the components of the earwax trap 2 of direct relevance to the present invention are

Figure 3A:
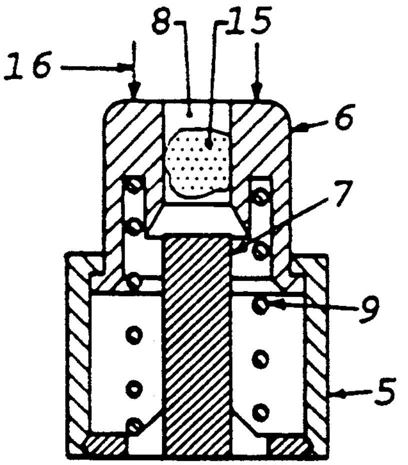
Figure 3B:
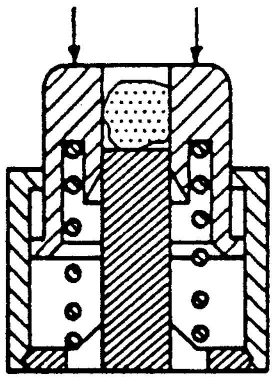
Figure 3C:
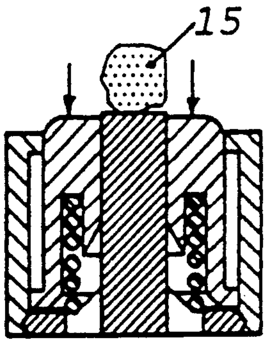
Figure 4A:
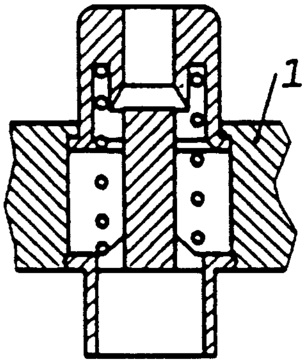
Figure 4B:
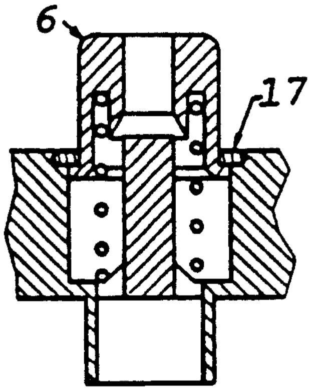
Figure 4C:
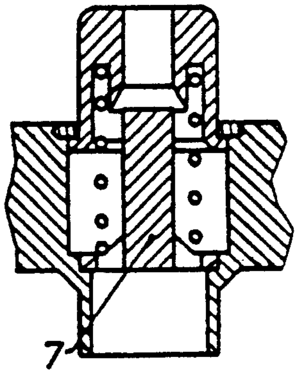
Figure 4D:
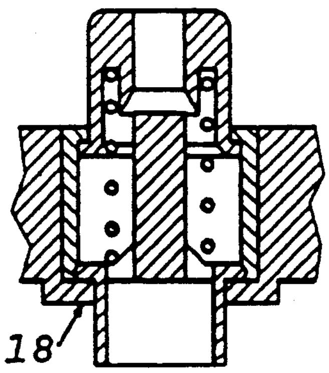
Figure 4E:
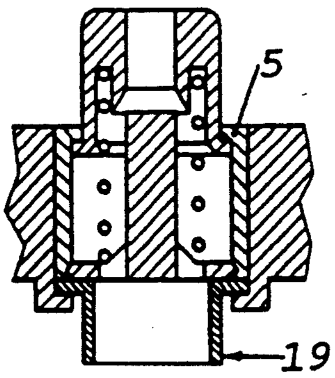
Figure 4F:
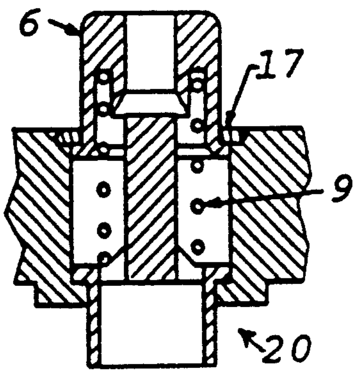

- a housing 5 adapted to be secured in the wall of the tip of the insertion portion 1 in the manner shown in FIG. 1, or—alternatively—to constitute a part of said wall,
- an earwax collector 6 slideably supported in the housing 5 between the normal operative position shown in FIG. 2 and a wax-removal position shown in FIG. 3*c*, and
- an earwax ejector 7, the cross-sectional shape of which corresponds at least roughly to the cross-sectional shape of a duct 8 formed and oriented in the earwax collector in such a manner, that when the earwax collector 6 is moved from the operating position shown in FIG. 2 to the wax-removal position shown in FIG. 3*c*, the duct 8 will be substantially fully occupied by and slideably receive the end portion of the earwax ejector 7, while a helical compression spring 9 constantly urges the earwax collector 6 towards the operating position shown in FIG. 2.

The sound-transmission path through the earwax trap 2 with the earwax collector 6 in the operating position shown in FIG. 2 consists of the space inside a tube connector 10 adapted to be connected with the connecting tube 4 shown in FIG. 1, at least one aperture 11 formed in a collar 12 surrounding and supporting the earwax ejector 7, a space 13 surrounding the ejector 7 and surrounded by the housing 5, an annular gap 14 between the tip of the ejector 7 and the adjacent part of the collector 6 surrounding the duct 8, and the duct 8 itself.

FIG. 3*a–c* shows how a lump of earwax 15 having collected in the earwax collector 6 is removed by simply pushing the earwax collector 6 into the housing 5 against the action of the spring 9, the force being represented by arrows 16 and suitably exerted by pressing two adjacent fingers onto the collector 6.

FIG. 3*a* shows the situation in the operating position shown also in FIG. 2, whereas FIG. 3*b* shows an intermediate situation, in which the collector 6 is partly depressed, and FIG. 3*c* shows the wax-removal position, in which the lump of earwax 15 lies freely accessible on the tip of the ejector 7 and can be removed without difficulty, such as by wiping it off with a piece of tissue or flicking it away with a finger.

FIGS. 4 *a–f* illustrate various possibilities in the practical realization of the present invention. Thus, in FIG. 4*a*, the housing 5 shown in FIG. 2 is replaced by the adjacent portion of the wall of the insertion portion 1, FIG. 4*b* shows an arrangement in which the tube connector 10 shown in FIG. 2 is replaced by a projecting flange on said wall and the outer limit for the movement of the earwax collector 6 is defined by a locking ring 17 inserted in said wall, FIG. 4*c* shows a similar arrangement but with an ejector 7 in the form of a separate part, FIG. 4*d* shows an arrangement corresponding to that of FIG. 2, inserted against a flange 18 formed in said wall, FIG. 4*e* shows an arrangement with a tube connector 19 in the form of a separate part, and FIG. 4*f* shows an arrangement, in which only four parts are inserted in a passage through said wall, i.e.

a combination 20 comprising both a tube connector and an earwax ejector, a spring 9, an earwax collector 6, and a locking ring 17.

It will be obvious to persons skilled in this art that the present invention may also be realized otherwise than shown in the drawing and explained above. Thus, an earwax collector 6 may comprise more than one duct 8, each adapted to cooperate with its own ejector 7 Further, the earwax trap need not necessarily be rotationally symmetrical as indicated in FIG. 2, but may be square, rectangular, or otherwise shaped as seen in cross section in a plane at right angles to the plane of the drawing in FIG. 2. The requisite relative movement between the earwax collector 6 and the earwax ejector 7 may also be achieved otherwise than shown and explained; thus, the collector 6 may be arranged stationary with respect to the insertion portion 1 and the ejector 7 moveable, or both components may be moveable in opposite directions. The essential requirement is, of course, that the transition between an operating position corresponding to that shown in FIG. 2 and wax-removal position corresponding to that shown in FIG. 3*c* always proceeds with the relative movement between the collector 6 and ejector 7 being such, that the latter moves towards the outside of the insertion portion 1, i.e. in a direction opposite the direction towards the receiver 3.

Figure 5A:
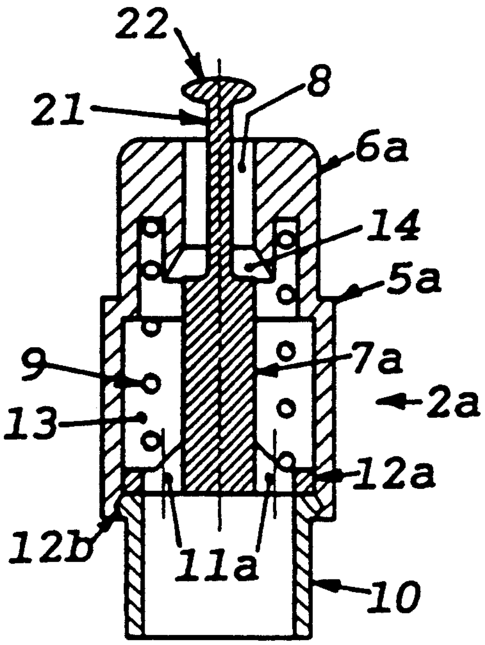
Figure 5B:
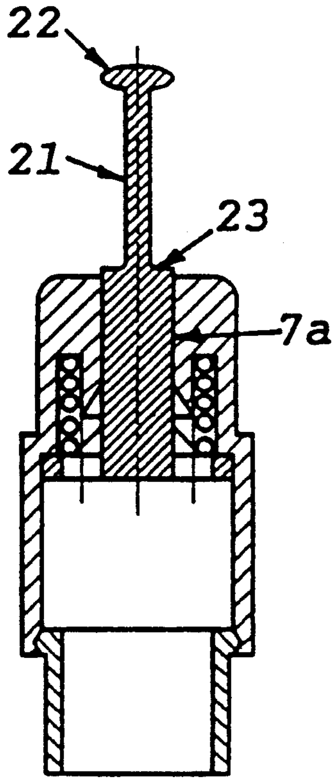

In the embodiment shown in FIG. 5, the earwax collector 6*a* is an integral part of the housing 5*a*, while the earwax ejector 7*a* is slidingly supported inside the housing 5*a* guided by the flange 12*a*, the latter being constantly urged in the downward (i.e. in operation inward) direction by the spring 9. To make it possible to move the earwax ejector 7*a* to the wax-removal position shown in FIG. 5*b*, a thin stem 21 with a knob 22 on its free end is formed integral with the ejector 7*a*. Any earwax (not shown) will collect on a shoulder 23 at the transition from the ejector 7*a* proper to the stem 21, and can easily be wiped off as described above with reference to FIG. 3*a*. Apertures 11*a* in the collar 12*a* allow the passage of sound coming through the ample clearance between the stem 21 and the walls of the duct 8, and a collar 12*b* on the tube connector 10 connects the latter to the housing 5*a*.

The earwax trap according to the present invention may be manufactured from any suitable material known to persons skilled in this art. Thus, the collectors 6, 6*a* and the ejectors 7, 7*a* may be made from a suitable plastics material (synthetic resin), while the spring 9 may suitably be made from spring steel. If for some reason it is considered undesirable to have metal components in the earwax trap, the spring 9 may be replaced by an elastic rubber bellows or the like placed close to the inside wall of the housing 5 or the corresponding part of the insertion portion 1.

In normal operation, any earwax collecting in the duct 8 can be removed from time to time by operating the trap in the manner described above. After prolonged periods of time, however, small amounts of earwax may have crept into the space 13, and for this reason it is desirable to make it possible to dismantle the trap or remove it bodily from the insertion portion 1. Persons skilled in this art will be able to devise methods of achieving this effect, not least after having seen FIGS. 4*a–f*.

The present invention is primarily intended for use with hearing-aid apparatus of the so-called in-the-ear (ITE) type, but may be used with the same effect with other types of hearing-aid apparatus, provided that these are adapted to deliver an acoustical signal into the external auditory meatus of the user. In this manner, the customary use of pipe cleaners and the like may be dispensed with.

I claim:

1. An earwax trap for use with hearing-aid apparatus, said trap comprising a) in a first part, a space adapted to provide an acoustic connection between an interior part of the hearing-aid apparatus and the external auditory meatus of the user's ear, and b) means for preventing earwax after having entered said space from leaving said space toward said interior part, said means comprising at least one piston- or plug-shaped member, which is adapted by relative movement between itself and the first part containing said space, to enter said space in a first direction away from said interior part of said hearing-aid apparatus, and to leave said space in a direction opposite to said first direction and thus re-establish the acoustic connection between said interior part and said space.

2. A trap according to claim 1, wherein said trap further comprises elastic means for urging said plug-shaped member towards a position relative to said first part containing said space, in which the plug-shaped member does not obstruct the acoustic communication between said interior part and said external auditory meatus, that the arrangement is said relative movement being caused by manually influencing said piston- or plug-shaped member and/or said first part containing said space or parts connected, and said relative position being resumed when said manual influence ceases.

3. A trap according to claim 2 wherein said trap includes a housing, said plug-shaped member being adapted to be stationary relative to the housing of the trap, and said first part containing said space being adapted to be moved relative thereto by being pushed into said housing.

4. A trap according to claim 2, wherein said trap includes a housing, said first part containing said space being adapted to be stationary relative to the housing of the trap, and said piston- or plug-shaped member being adapted to be moved relative thereto by being pulled out of said housing, and comprising an externally accessible extension extending outwardly with ample clearance through said space.

5. A trap according to claim 1 wherein said trap is adapted to be used with a hearing-aid apparatus including an insertion portion having a wall and said trap is adapted to be inserted into the wall of the insertion portion of the hearing-aid apparatus, said insertion portion being adapted to be inserted into the external auditory meatus of the user's ear.

6. A trap according to claim 1 wherein the trap is adapted to be used with a hearing-aid apparatus including an insertion portion having a wall and said trap is at least partly integral with the wall of the insertion portion of the hearing-aid apparatus, said insertion portion being adapted to be inserted into the external auditory meatus of the user's ear.

7. A hearing-aid apparatus with an earwax trap, said earwax trap comprising a) in a first part a space adapted to provide an acoustic connection between an interior part of the hearing-aid apparatus and the external auditory meatus of the user's ear, and b) means for preventing earwax after having entered said space from leaving said space towards said interior part, said means comprising at least one piston- or plug-shaped member, which is adapted by relative movement between itself and the first part containing said space, to enter said space in a first direction away from said interior part of said hearing-aid apparatus, and to leave said space in a direction opposite to said first direction and thus reestablish the acoustic connection between said interior part and said space.

8. A hearing-aid apparatus as claimed in claim 7, wherein said trap further comprises elastic means for urging said plug-shaped member towards a position relative to said first part containing said space, in which the plug-shaped member does not obstruct the acoustic communication between said interior part and said external auditory meatus, said relative movement being caused by manually influencing said piston- or plug-shaped member and/or said first part containing said space, and said relative position being resumed when said manual influence ceases.

9. A hearing-aid apparatus as claimed in claim 8, wherein said trap includes a housing, said plug-shaped member being adapted to be stationary relative to the housing of the trap, and said first part containing said space being adapted to be moved relative thereto by being pushed into said housing.

10. A hearing-aid apparatus as claimed in claim 8, wherein said trap includes a housing, said first part containing said space being adapted to be stationary relative to the housing of the trap, and said piston- or plug-shaped member being adapted to be moved relative thereto by being pulled out of said housing, and comprising an externally accessible extension extending outwardly with ample clearance through said space.

11. A hearing-aid apparatus as claimed in claim 7, wherein said hearing-aid apparatus includes an insertion portion having a wall and said trap is adapted to be inserted into the wall of the insertion portion of the hearing-aid apparatus, said insertion portion being adapted to be inserted into the external auditory meatus of the user's ear.

12. A hearing-aid apparatus as claimed in claim 7, wherein said hearing-aid apparatus includes an insertion portion having a wall and said trap is at least partly integral with the wall of the insertion portion of the hearing-aid apparatus, said insertion portion being adapted to be inserted into the external auditory meatus of the user's ear.

* * * * *